(12) United States Patent
Tang et al.

(10) Patent No.: US 11,941,160 B2
(45) Date of Patent: Mar. 26, 2024

(54) CABLE FORCE ADJUSTMENT

(71) Applicant: Baker Hughes Oilfield Operations LLC, Houston, TX (US)

(72) Inventors: Andrew Lee Tang, Houston, TX (US); Bryan Christopher Morris, Skaneateles, NY (US); James J. Delmonico, Skaneateles, NY (US)

(73) Assignee: Baker Hughes Oilfield Operations LLC, Houston, TX (US)

( * ) Notice: Subject to any disclaimer, the term of this patent is extended or adjusted under 35 U.S.C. 154(b) by 0 days.

(21) Appl. No.: 18/170,956

(22) Filed: Feb. 17, 2023

(65) Prior Publication Data

US 2023/0205308 A1 Jun. 29, 2023

Related U.S. Application Data

(63) Continuation of application No. 16/738,803, filed on Jan. 9, 2020, now Pat. No. 11,586,275.

(51) Int. Cl.
*G06F 3/00* (2006.01)
*G01L 5/00* (2006.01)

(52) U.S. Cl.
CPC .............. *G06F 3/00* (2013.01); *G01L 5/0042* (2013.01)

(58) Field of Classification Search
CPC ..... G06F 3/00; G01L 5/0042; A61B 1/00006; A61B 1/0057; H02P 6/08; H02P 23/12
See application file for complete search history.

(56) References Cited

U.S. PATENT DOCUMENTS

| | | | |
|---|---|---|---|
| 7,134,993 B2 * | 11/2006 | Lia | A61B 1/05 600/149 |
| 9,505,132 B1 * | 11/2016 | Bingham | B25J 9/1694 |
| 10,155,316 B2 * | 12/2018 | Wakai | A61B 34/71 |
| 11,586,275 B2 * | 2/2023 | Tang | G06F 3/00 |
| 2005/0168571 A1 * | 8/2005 | Lia | G02B 23/24 348/82 |
| 2016/0361819 A1 * | 12/2016 | Wakai | A61B 1/00057 |
| 2021/0213628 A1 * | 7/2021 | Tang | A61B 1/00006 |

* cited by examiner

*Primary Examiner* — Freddie Kirkland, III
(74) *Attorney, Agent, or Firm* — Mintz, Levin, Cohn, Ferris, Glovsky and Popeo PC (57) ABSTRACT

A method includes transmitting an instruction to a motive power supply of an elastically deformable device to drive the elastically deformable device in accordance with a drive setting; measuring a force exerted on the elastically deformable device with a sensor; outputting an observed value representative of the force; comparing the observed value with a reference value corresponding with a predetermined force to be exerted on the elastically deformable device; and adjusting the drive setting based on a determination that the observed value is outside of a predetermined range of the reference value. The method prevents slack in the elastically deformable device over time. Related apparatuses, systems, techniques and articles are also described.

18 Claims, 6 Drawing Sheets

CABLE FORCE ADJUSTMENT

CROSS-REFERENCE TO RELATED APPLICATIONS

This application is a continuation of U.S. patent application Ser. No. 16/738,803 filed Jan. 9, 2020 and entitled "CABLE FORCE ADJUSTMENT," the entire contents of which are hereby expressly incorporated by reference herein.

BACKGROUND

The field of this disclosure relates to cable force adjustment, which may be used in the fields of sensors, analytics, signal processing, machinery diagnostics, condition monitoring, and related disciplines. Remote borescope inspection tools are utilized to identify and/or predict equipment failures in the field of industrial equipment in industries such as aerospace, power generation, oil and gas, automotive, food and beverage, and pharmaceutical manufacturing. For example, borescope inspection tools are used to inspect pumps, motors, generators, pulp and paper rollers, gear boxes, pipes, tubes, purity pipes, compressors, large pistons, chillers, valves, gun barrels, mortar tubes, vehicles, shipping containers, and maritime surveying structures.

SUMMARY

A method including: transmitting an instruction to a motive power supply of an elastically deformable device to drive the elastically deformable device in accordance with a drive setting; measuring a force exerted on the elastically deformable device with a sensor; outputting an observed value representative of the force; comparing the observed value with a reference value corresponding with a predetermined force to be exerted on the elastically deformable device; and adjusting the drive setting based on a determination that the observed value is outside of a predetermined range of the reference value.

The method may further include repeating the method beginning at the measuring of the force.

The method may be provided so that the adjusting of the drive setting includes: increasing the drive setting based on a determination that the observed value is less than a lower threshold of the predetermined range of the reference value, decreasing the drive setting based on a determination that the observed value is greater than an upper threshold of the predetermined range of the reference value, and maintaining the drive setting based on a determination that the observed value is greater than or equal to the lower threshold and less than or equal to the upper threshold.

The method may be provided so that the motive power supply includes a motor, the elastically deformable device includes a cable, the force includes tension on the cable, and the sensor includes a potentiometer.

The method may be provided so that the reference value is set at zero based on detection of a desired tension of the cable.

The method may be provided so that the drive setting corresponds with a motor force exerted by the motor on the cable sufficient to maintain the potentiometer within the predetermined range of the reference value.

The method may be provided so that the cable is a steering cable for a borescope.

The method may be provided so that the motive power supply is one from the group consisting of a servo, a micromotor, a linear motor, a lead screw motor, a pneumatic actuator, a solenoid, shape memory alloys, a dielectric actuator, a polymer elastic actuator, a piezo-electric motor, and a stepper, and wherein the sensor is one from the group consisting of a Hall effect sensor, a photo-interrupt sensor, a rotary encoder sensor, a force transducer, an optical sensor, a linear induction sensor, and a digital sensor with optical encoding.

The method may be provided so that the measuring, outputting, comparing, and adjusting are performed on a timed schedule of once per 10 ms.

A system, including: at least one processor and a memory storing at least one program for execution by the at least one processor, the at least one program including instructions, which when executed by the at least one processor cause the at least one processor to perform operations including: transmitting an instruction to a motive power supply of an elastically deformable device to drive the elastically deformable device in accordance with a drive setting; measuring a force exerted on the elastically deformable device with a sensor; outputting an observed value representative of the force; comparing the observed value with a reference value corresponding with a predetermined force to be exerted on the elastically deformable device; and adjusting the drive setting based on a determination that the observed value is outside of a predetermined range of the reference value.

The system may further include: an elastically deformable device; a motive power supply configured to drive the elastically deformable device; and a sensor configured to quantify the force exerted on the elastically deformable device.

The system may further include repeating the operations beginning at the measuring of the force.

The system may be provided so that the adjusting of the drive setting includes: increasing the drive setting based on a determination that the observed value is less than a lower threshold of the predetermined range of the reference value, decreasing the drive setting based on a determination that the observed value is greater than an upper threshold of the predetermined range of the reference value, and maintaining the drive setting based on a determination that the observed value is greater than or equal to the lower threshold and less than or equal to the upper threshold.

The system may be provided so that the motive power supply includes a motor, the elastically deformable device includes a cable, the force includes tension on the cable, and the sensor includes a potentiometer.

The system may be provided so that the reference value is set at zero based on detection of a desired tension of the cable.

The system may be provided so that the drive setting corresponds with a motor force exerted by the motor on the cable sufficient to maintain the potentiometer within the predetermined range of the reference value.

The system may be provided so that the cable is a steering cable for a borescope.

The system may be provided so that the motive power supply is one from the group consisting of a servo, a micromotor, a linear motor, a lead screw motor, a pneumatic actuator, a solenoid, shape memory alloys, a dielectric actuator, a polymer elastic actuator, a piezo-electric motor, and a stepper, and wherein the sensor is one from the group consisting of a Hall effect sensor, a photo-interrupt sensor, a rotary encoder sensor, a force transducer, an optical sensor, a linear induction sensor, and a digital sensor with optical encoding.

The system may be provided so that the measuring, outputting, comparing, and adjusting are performed on a timed schedule of once per 10 ms.

A non-transitory computer-readable storage medium storing at least one program, which when executed by at least one processor and a memory storing the at least one program cause the at least one processor to perform operations including: transmitting an instruction to a motive power supply of an elastically deformable device to drive the elastically deformable device in accordance with a drive setting; measuring a force exerted on the elastically deformable device with a sensor; outputting an observed value representative of the force; comparing the observed value with a reference value corresponding with a predetermined force to be exerted on the elastically deformable device; and adjusting the drive setting based on a determination that the observed value is outside of a predetermined range of the reference value.

The non-transitory computer-readable storage medium may further include repeating the operations beginning at the measuring of the force.

The non-transitory computer-readable storage medium may be provided so that the adjusting of the drive setting includes: increasing the drive setting based on a determination that the observed value is less than a lower threshold of the predetermined range of the reference value, decreasing the drive setting based on a determination that the observed value is greater than an upper threshold of the predetermined range of the reference value, and maintaining the drive setting based on a determination that the observed value is greater than or equal to the lower threshold and less than or equal to the upper threshold.

The non-transitory computer-readable storage medium may be provided so that the motive power supply includes a motor, the elastically deformable device includes a cable, the force includes tension on the cable, and the sensor includes a potentiometer.

The non-transitory computer-readable storage medium may be provided so that the reference value is set at zero based on detection of a desired tension of the cable.

The non-transitory computer-readable storage medium may be provided so that the drive setting corresponds with a motor force exerted by the motor on the cable sufficient to maintain the potentiometer within the predetermined range of the reference value.

The non-transitory computer-readable storage medium may be provided so that the cable is a steering cable for a borescope.

The non-transitory computer-readable storage medium may be provided so that the motive power supply is one from the group consisting of a servo, a micromotor, a linear motor, a lead screw motor, a pneumatic actuator, a solenoid, shape memory alloys, a dielectric actuator, a polymer elastic actuator, a piezo-electric motor, and a stepper, and wherein the sensor is one from the group consisting of a Hall effect sensor, a photo-interrupt sensor, a rotary encoder sensor, a force transducer, an optical sensor, a linear induction sensor, and a digital sensor with optical encoding.

The non-transitory computer-readable storage medium may be provided so that the measuring, outputting, comparing, and adjusting are performed on a timed schedule of once per 10 ms.

These and other capabilities of the disclosed subject matter will be more fully understood after a review of the following figures, detailed description, and claims.

DESCRIPTION OF DRAWINGS

These and other features will be more readily understood from the following detailed description taken in conjunction with the accompanying drawings, in which.

It is noted that the drawings are not necessarily to scale. The drawings are intended to depict only typical aspects of the subject matter disclosed herein, and therefore should not be considered as limiting the scope of the disclosure. The structures, systems, devices, and methods specifically described herein and illustrated in the accompanying drawings are non-limiting exemplary embodiments and that the scope of the present invention is defined solely by the claims.

DETAILED DESCRIPTION

Over time, conventional borescopes develop cable slack as a product of insertion tube compression and cable stretch. As the slack develops, there becomes a point where motors, which have a limited stroke, cannot take up the extra cable. As a result, articulation and responsiveness of the borescope are lost over time. To overcome these problems, a sensor is attached to a steering cable that senses when the cable is taut. Feedback from the sensor is used by a steering system to determine when to utilize more stroke as cable slack develops. The steering system effectively adapts over time and extends the useful life of the system.

With conventional borescopes, a motor having a stroke of +/−0.20 in to 0.50 in (5.08 mm to 12.7 mm) was typical. A motor capable of generating more stroke may be provided. A sensor may be provided configured to send signals to a processor to determine when the motor should use more stroke over time.

Since cable slack develops over relatively long periods of time (e.g., in extreme conditions, slack may start to occur around 6 months; with light use, slack may take several years or longer to develop), at installation, a motor may require a relatively low amount of stroke (e.g., on the order of +/−0.20" to 0.50" (5.08 mm to 12.7 mm)). Also, the slack problem is more pronounced with relatively long cables. Typical borescopes cables are about 6.56 ft to 32.8 ft (2 m to 10 m) in length. Slack is more noticeable at, for example, 14.8 ft (4.5 m) or longer compared to 6.56 ft (2 m). Slack develops when the cables permanently stretch and the insertion tube compresses over time with use.

To compensate for differences over time, including the slack problem, the motor may be provisioned at installation with a relatively large amount of potential stroke to adjust to changes in cable slack over time. In some embodiments for borescope applications, the stroke of the motor may be on the order of +/−0.45 in to 1.00 in (11.43 mm to 25.4 mm), an increase of approximately 50% to 100% relative to conventional motors. Other suitable motors may be employed, depending on the application. In relatively larger scale applications, the stroke of the motor may be on the order of +/−2.20 in to 10.50 in (55.88 mm to 266.7 mm).

The system monitors and determines when to utilize additional amounts of stroke over time. A mechanical device may be used to couple the steering cable system to a potentiometer. The potentiometer may be configured to calibrate a "zero" position for each direction. The sensor or potentiometer may utilize sensing technologies including Hall effect, linear induction, optical, digital with optical encoding, and the like. The motor may be configured to turn until the cable moves the potentiometer to the zero position. At this point, at the zero position, all stroke that is used is "useful stroke", i.e., stroke that moves the bending neck. Over time, as slack develops, more and more stroke is required to reach the zero position. The sensors may be configured to detect increasing (or decreasing) slack, and the motors may be configured to activate to adjust the system until the potentiometer returns to the zero position.

In some embodiments, at initial use of a borescope, a camera may be provided in line with an insertion tube, which is a home position for the camera. In the home position, a potentiometer (e.g., potentiometer 100, FIGS. 4 and 5) is provided at a nominal center position, and a cable slack is either zero or equally distributed between two cables. As the camera is steered away from center, tension increases on one cable while the other cable becomes slack. As slack occurs, a block (e.g., block 150, FIG. 6) with attached cable sheath terminators move up following the cable in tension, which results in the potentiometer moving off nominal center. The camera may be moved in the opposite direction, and the block will begin to move toward the previously slack cable when the slack is taken up. The potentiometer senses the slack in the cable. A system (e.g., system 10, FIG. 1) receives data from the potentiometer, and processes the received data to compensate for the cable slack. As shown, for example, in FIG. 5, a rotary follower and rotary potentiometer may be used.

Figure 1:
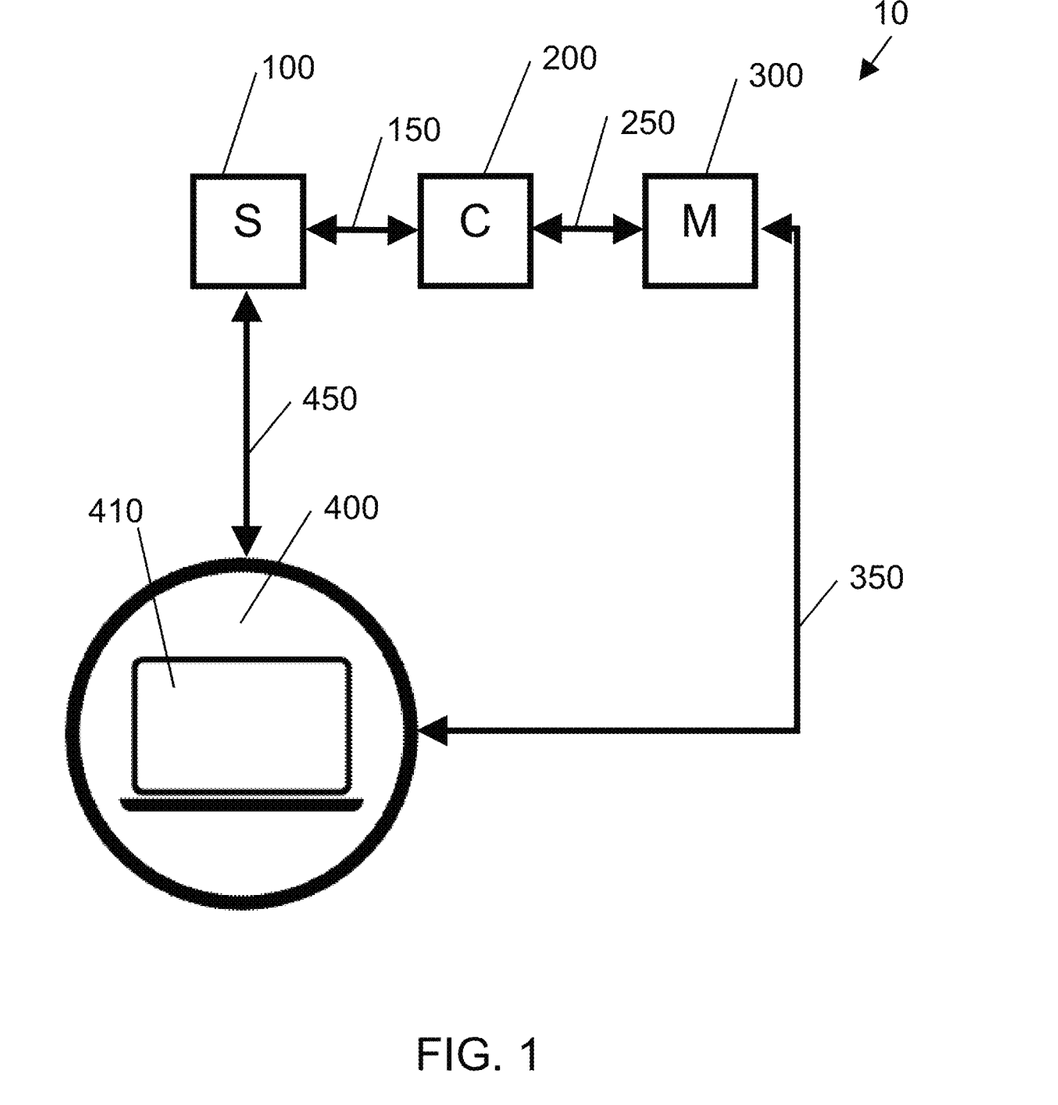
FIG. 1 is a schematic diagram of a system for adjusting a force exerted on an elastically deformable device.

In one exemplary implementation, as shown in FIG. 1, a system 10 for adjusting a force exerted is provided. The system 10 may include an elastically deformable device 200. The elastically deformable device 200 may be a cable, a steering cable for a borescope, a linkage, a chain, a string, a rope, a fiber, and the like. The system 10 may include a motive power supply 300 configured to drive the elastically deformable device 200. For the motive power supply 300, various motors may be used including a servo, a micromotor, a linear motor, a lead screw motor, a pneumatic actuator, a solenoid, shape memory alloys, a dielectric or polymer elastic actuator, a piezo-electric motor, a stepper, and the like. The motive power supply 300 may be directly connected to the elastically deformable device 200 or indirectly connected to the elastically deformable device 200 via a connecting structure 250.

The system 10 may include a sensor 100. The sensor 100 may be configured to quantify a force exerted on the elastically deformable device 200. The force may be tension, compression, torque, and the like. For the sensor 100, various sensors may be used including a Hall effect sensor, a photo-interrupt sensor, a rotary encoder sensor, a force transducer and an optical sensor. The sensor may be integrated into the motive power supply 300. The sensor 100 may be provided separately from the motive power supply 300, as illustrated in FIG. 1. The sensor 100 may be installed directly on the elastically deformable device 200. The sensor 100 may be indirectly connected to the elastically deformable device 200 via a connecting structure 150. The system 10 may include a computing device such as the device or system 500 illustrated in FIG. 3.

Figure 3:
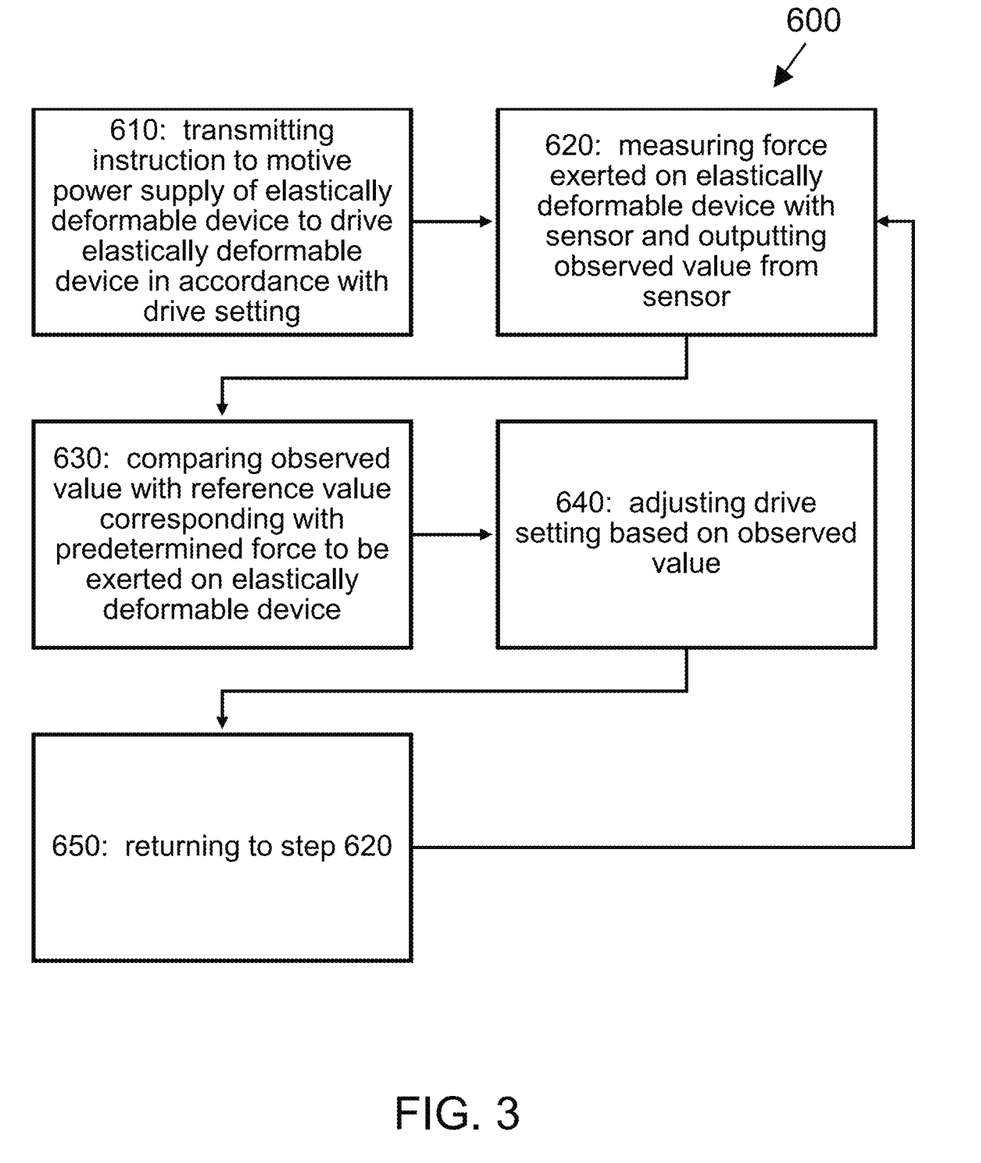
FIG. 3 is a process diagram illustrating a method of adjusting a force exerted on an elastically deformable device.

FIG. 3 depicts a device or system 500 comprising at least one processor 530 and a memory 540 storing at least one program 550 for execution by the at least one processor 530. In some implementations, the device or system 500 may further comprise a non-transitory computer-readable storage medium 560 storing the at least one program 550 for execution by the at least one processor 530 of the device or system 500. In some implementations, the device or system 500 may further comprise at least one input device 510, which may be configured to send or receive information to or from any one from the group consisting of: an external device (not shown), the at least one processor 530, the memory 540, the non-transitory computer-readable storage medium 560, and at least one output device 570. The at least one input device 510 may be configured to wirelessly send or receive information to or from the external device via a means for wireless communication, such as an antenna 520, a transceiver (not shown) or the like.

In some implementations, the device or system 500 may further comprise at least one output device 570, which may be configured to send or receive information to or from any one from the group consisting of: an external device (not shown), the at least one input device 510, the at least one processor 530, the memory 540, and the non-transitory computer-readable storage medium 560. The at least one output device 570 may be configured to wirelessly send or receive information to or from the external device via a means for wireless communication, such as an antenna 580, a transceiver (not shown) or the like.

The program 550 may include operations 600. The operations 600 may include a step 610 of transmitting an instruction to a motive power supply of the elastically deformable device to drive the elastically deformable device in accordance with a drive setting; a step 620 of measuring the force exerted on the elastically deformable device with a sensor and outputting an observed value from the sensor; a step 630 of comparing the observed value with a reference value corresponding with a predetermined force to be exerted on the elastically deformable device; a step 640 of adjusting the drive setting based on the observed value; and a step 650 of returning to step 620. The step 640 may include a behavioral model of the insertion tube and cable system. The model may represent the behavior of the cable and insertion tube under various levels of tension. The model may also take into account age or extreme usage of the steering mechanism or environmental conditions such as temperature and humidity.

One or more of steps 620, 630, 640 and 650 may be periodically performed on a timed schedule. For example, in some embodiments, steps 620, 630, 640 and 650 may be periodically performed on the order of once per 10 ms (0.01 sec). In some embodiments, steps 620, 630, 640 and 650 may be performed in shorter increments, longer increments or continuously. One or more operations 600 may be manually initiated by a user of the system 10.

Figure 4:
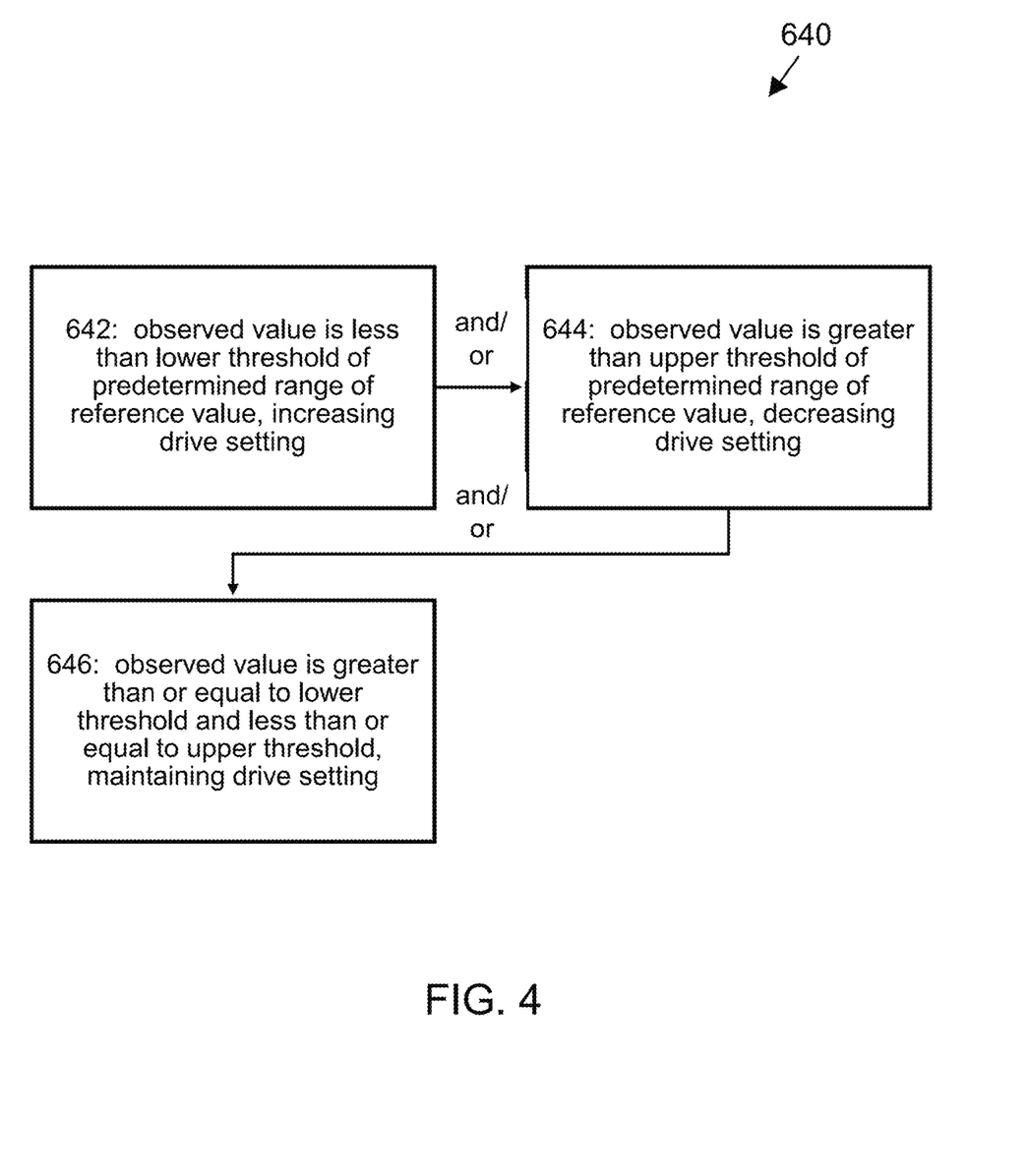
FIG. 4 is a process diagram illustrating conditions of an adjusting step of the method of adjusting the force exerted on the elastically deformable device.

As seen in FIG. 4, step 640 may include a step 642, the observed value is less than a lower threshold of the predetermined range of the reference value, increasing the drive setting, and/or step 644, the observed value is greater than an upper threshold of the predetermined range of the reference value, decreasing the drive setting, and/or step 646, the observed value is greater than or equal to the lower threshold and less than or equal to the upper threshold, maintaining the drive setting.

In some embodiments, the system may adjust the cables using a rotary follower (e.g., follower 150, FIG. 5) moved in increments of +/−1/10 of a degree (+/−0.1°). Finer and coarser adjustment increments may be used.

Figure 5:
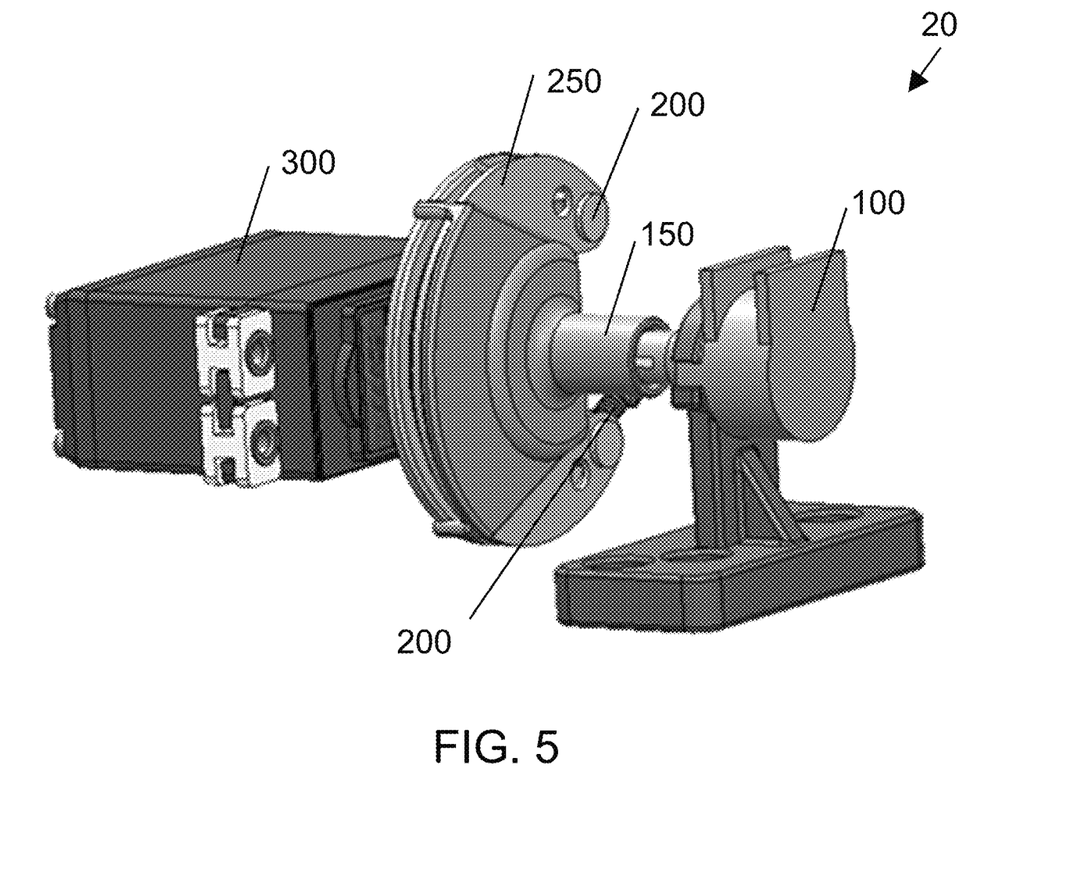
FIG. 5 is a perspective view of a system according to one exemplary embodiment.

FIG. 5 illustrates an example of a system 20 including a servo 300. The servo 300 may rotate a cam 250 configured to attach and pull cables 200. The cables 200 may rotate a follower 150. The follower 150 may be coupled to a rotary potentiometer 100.

Figure 6:
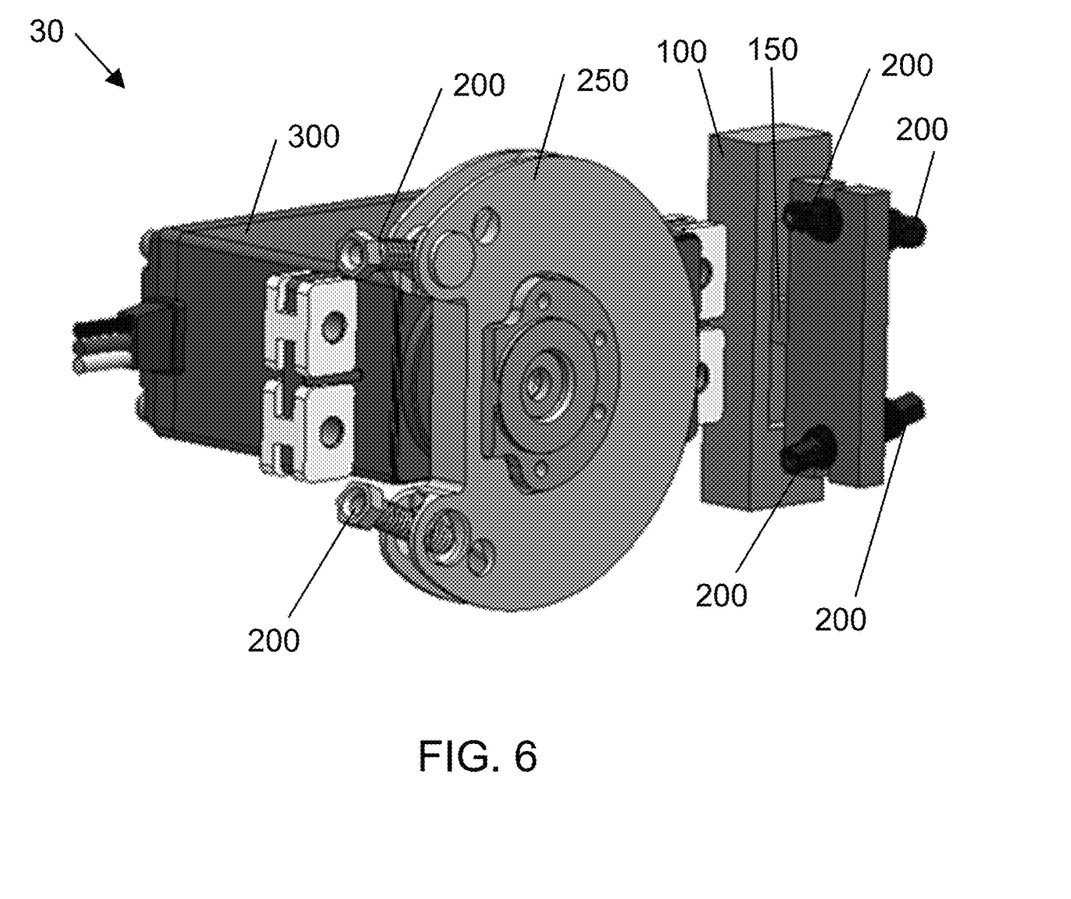
FIG. 6 is a perspective view of a system according to another exemplary embodiment.

FIG. 6 illustrates an example of a system 30 including a servo 300. The servo 300 may rotate a cam 250 configured to attach and pull cables 200. The cables 200 may move a block 150. The block 150 may be coupled to a slide potentiometer 100.

Figure 2:
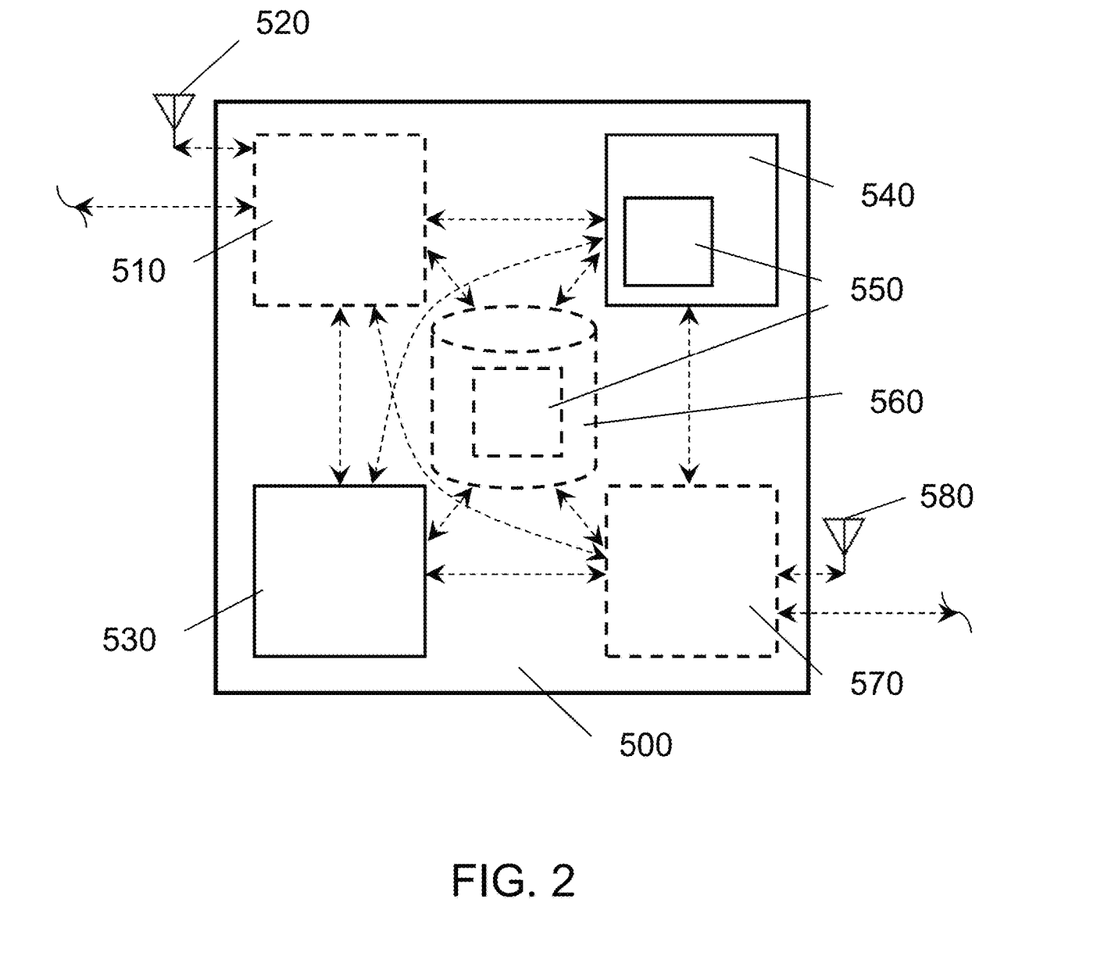
FIG. 2 is a schematic depiction of a computer device or system including at least one processor and a memory storing at least one program for execution by the at least one processor.

Each of the system 20 and the system 30 may include one or more features of the system 10 (FIG. 1), the device or system 500 (FIG. 2), and the operations 600 (FIG. 3), including the step 640 (FIG. 4).

As used herein, slack may be, for example, a lack of tension on a cable. The sensor may sense a lack of tension and the system may be configured to respond to the detection of the lack of tension. Tension may be detected using a potentiometer configured to measure tension or lack of tension in units of volts (V), or Ohms (Ω). The system may be configured to detect improper pre-tensioning during manufacturing.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Although at least one exemplary embodiment is described as using a plurality of units to perform the exemplary process, it is understood that the exemplary processes may also be performed by one or plurality of modules. Additionally, it is understood that the term controller/control unit may refer to a hardware device that includes a memory and a processor. The memory may be configured to store the modules and the processor may be specifically configured to execute said modules to perform one or more processes which are described further below.

The use of the terms "first", "second", "third" and so on, herein, are provided to identify various structures, dimensions or operations, without describing any order, and the structures, dimensions or operations may be executed in a different order from the stated order unless a specific order is definitely specified in the context.

Approximating language, as used herein throughout the specification and claims, may be applied to modify any quantitative representation that could permissibly vary without resulting in a change in the basic function to which it is related. Accordingly, a value modified by a term or terms, such as "about" and "substantially," are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Furthermore, control logic of the present disclosure may be embodied as non-transitory computer readable media on a computer readable medium containing executable program instructions executed by a processor, controller/control unit or the like. Examples of the computer readable mediums include, but are not limited to, ROM, RAM, compact disc (CD)-ROMs, magnetic tapes, floppy disks, flash drives, smart cards and optical data storage devices. The computer readable recording medium can also be distributed in network coupled computer systems so that the computer readable media is stored and executed in a distributed fashion, e.g., by a telematics server or a Controller Area Network (CAN).

One or more aspects or features of the subject matter described herein may be realized in digital electronic circuitry, integrated circuitry, specially designed application specific integrated circuits (ASICs), field programmable gate arrays (FPGAs) computer hardware, firmware, software, and/or combinations thereof. These various aspects or features may include embodiment in one or more computer programs that are executable and/or interpretable on a programmable system including at least one programmable processor, which may be special or general purpose, coupled to receive data and instructions from, and to transmit data and instructions to, a storage system, at least one input device, and at least one output device. The programmable system or computing system may include clients and servers. A client and server are substantially remote from each other and typically interact through a communication network. The relationship of client and server arises by virtue of computer programs running on the respective computers and having a client-server relationship to each other.

These computer programs, which may also be referred to as programs, software, software applications, applications, components, or code, include machine instructions for a programmable processor, and may be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium may store such machine instructions non-transitorily, such as for example as would a non-transient solid-state memory or a magnetic hard drive or any equivalent storage medium. The machine-readable medium may alternatively or additionally store such machine instructions in a transient manner, such as for example as would a processor cache or other random access memory associated with one or more physical processor cores.

To provide for interaction with a user, one or more aspects or features of the subject matter described herein may be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices may be used to provide for interaction with a user as well. For example, feedback provided to the user may be any form of sensory feedback, such as for example visual feedback, auditory feedback, or tactile feedback; and input from the user may be received in any form, including acoustic, speech, or tactile input. Other possible input devices include touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

The subject matter described herein may be embodied in systems, apparatus, methods, and/or articles depending on the desired configuration. The embodiments set forth in the foregoing description do not represent all embodiments consistent with the subject matter described herein. Instead, they are merely some examples consistent with aspects related to the described subject matter. Although a few variations have been described in detail above, other modifications or additions are possible. In particular, further features and/or variations may be provided in addition to those set forth herein. For example, the embodiments described above may be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other embodiments may be within the scope of the following claims.

What is claimed is:

1. A method of comprising:
    transmitting an instruction to a motive power supply of an elastically deformable device to drive the elastically deformable device in accordance with a drive setting defined by one or more zero positions of the elastically deformable device;
    measuring, with a sensor, one or more forces exerted on the elastically deformable device at the one or more zero positions;
    increasing an amount of stroke used by the motive power supply responsive to determining that the one or more forces are less than a predetermined range;
    maintaining the amount of stroke responsive to determining that the one or more forces are within to the predetermined range; and
    decreasing the amount of stroke responsive to determining that the one or more forces are greater than the predetermined range.

2. The method of claim 1, further comprising repeating the method beginning at the measuring of the one or more forces.

3. The method of claim 1, wherein the motive power supply includes a motor, the elastically deformable device includes a cable, and the one or more forces are defined by tension in the cable.

4. The method of claim 3, wherein the predetermined range is determined based on a desired amount of tension in the cable.

5. The method of claim 3, wherein the cable is a steering cable for a borescope.

6. The method of claim 3, wherein the sensor is a potentiometer.

7. The method of claim 1, wherein the motive power supply is one from the group consisting of a servo, a micromotor, a linear motor, a lead screw motor, a pneumatic actuator, a solenoid, shape memory alloys, a dielectric actuator, a polymer elastic actuator, a piezo-electric motor, and a stepper, and
    wherein the sensor is one from the group consisting of a Hall effect sensor, a photo-interrupt sensor, a rotary encoder sensor, a force transducer, an optical sensor, a linear induction sensor, and a digital sensor with optical encoding.

8. The method of claim 1, wherein the measuring and the increasing, maintaining, or decreasing are performed on a timed schedule of once per 10 ms.

9. A system, comprising:
    at least one processor and a memory communicably coupled to the at least one processor, the memory storing non-transitory computer-readable instructions, which when executed by the at least one processor cause the at least one processor to perform operations comprising:
    transmitting an instruction to a motive power supply of an elastically deformable device to drive the elastically deformable device in accordance with a drive setting defined by one or more zero positions of the elastically deformable device;
    measuring, with a sensor, one or more forces exerted on the elastically deformable device at the one or more zero positions;
    increasing an amount of stroke used by the motive power supply responsive to determining that the one or more forces are less than a predetermined range;
    maintaining the amount of stroke responsive to determining that the one or more forces are within to the predetermined range;
    and decreasing the amount of stroke responsive to determining that the one or more forces are greater than the predetermined range.

10. The system of claim 9, the system further comprising:
the elastically deformable device;
the motive power supply configured to drive the elastically deformable device; and
the sensor configured to quantify the one or more forces exerted on the elastically deformable device.

11. The system of claim 10, further comprising repeating the operations beginning at the measuring of the force.

12. The system of claim 9, wherein the motive power supply includes a motor, the elastically deformable device includes a cable, and the one or more forces are defined by tension in the cable.

13. The system of claim 12, wherein the predetermined range is determined based on a desired amount of tension in the cable.

14. The system of claim 12, wherein the cable is a steering cable for a borescope.

15. The system of claim 12, wherein the sensor is a potentiometer.

16. The system of claim 9, wherein the motive power supply is one from the group consisting of a servo, a micromotor, a linear motor, a lead screw motor, a pneumatic actuator, a solenoid, shape memory alloys, a dielectric actuator, a polymer elastic actuator, a piezo-electric motor, and a stepper, and
wherein the sensor is one from the group consisting of a Hall effect sensor, a photo-interrupt sensor, a rotary encoder sensor, a force transducer, an optical sensor, a linear induction sensor, and a digital sensor with optical encoding.

17. The system of claim 9, wherein the measuring and the increasing, maintaining, or decreasing are performed on a timed schedule of once per 10 ms.

18. A non-transitory computer-readable storage medium communicably coupled to at least one processor, wherein the non-transitory computer-readable storage medium stores computer-readable instructions, which when executed by at least one processor cause the at least one processor to perform operations comprising:
transmitting an instruction to a motive power supply of an elastically deformable device to drive the elastically deformable device in accordance with drive setting defined by one or more zero positions of the elastically deformable device;

measuring, with a sensor, one or more forces exerted on the elastically deformable device at the one or more zero positions;

increasing an amount of stroke used by the motive power supply responsive to determining that the one or more forces are less than a predetermined range;

maintaining the amount of stroke responsive to determining that the one or more forces are within to the predetermined range; and decreasing the amount of stroke responsive to determining that the one or more forces are greater than the predetermined range.

* * * * *